US009393569B2

(12) United States Patent
Morgan et al.

(10) Patent No.: US 9,393,569 B2
(45) Date of Patent: Jul. 19, 2016

(54) INTEGRATED MEDICAL WASTE MANAGEMENT SYSTEM AND OPERATION

(71) Applicant: SteriMed Medical Waste Solutions UK Ltd., Surrey (GB)

(72) Inventors: Dwight Morgan, West Bloomfield, MI (US); Meir Weiss, Gilboa (IL); Boris Indych, Afula (IL); Yuri Litinsky, Afula (IL)

(73) Assignee: SteriMed Medical Waste Solutions UK Ltd., Haslemere (GB)

( * ) Notice: Subject to any disclaimer, the term of this patent is extended or adjusted under 35 U.S.C. 154(b) by 168 days.

(21) Appl. No.: 13/737,461

(22) Filed: Jan. 9, 2013

(65) Prior Publication Data

US 2013/0175373 A1   Jul. 11, 2013

Related U.S. Application Data

(60) Provisional application No. 61/585,022, filed on Jan. 10, 2012.

(51) Int. Cl.
*B02C 23/00* (2006.01)
*B02C 23/36* (2006.01)
(Continued)

(52) U.S. Cl.
CPC .................. *B02C 23/00* (2013.01); *A61L 2/186* (2013.01); *A61L 11/00* (2013.01); *B02C 19/0075* (2013.01); *B02C 23/08* (2013.01); *B02C 23/12* (2013.01);
(Continued)

(58) Field of Classification Search
CPC .. B02C 19/0075; B02C 19/186; B02C 25/00; B02C 18/0084; B02C 23/24; B02C 23/36; B02C 23/00; B02C 23/18; B02C 23/12; B02C 23/40; B02C 23/08; A61L 11/00; A61L 2/04; A61L 2202/14; B09B 3/0075
USPC ............. 241/606, 33–36, 79, 79.1, 21, 101.4, 241/101.2, 65–66
See application file for complete search history.

(56) References Cited

U.S. PATENT DOCUMENTS 3,750,847 A * 8/1973 Sluhan ......................... 184/109
4,621,773 A * 11/1986 Calevich et al. ................ 241/21
(Continued)

FOREIGN PATENT DOCUMENTS

EP          0597779        5/1994
EP          0908189        4/1999
(Continued)

*Primary Examiner* — Mark Rosenbaum
(74) *Attorney, Agent, or Firm* — Dinsmore & Shohl LLP

(57) ABSTRACT

An integrated medical waste management and treatment system may include sensors, interlocks, communications links and/or other features for determining if the waste itself, the decontaminating disinfectant used in the process, or the status of the system are consistent with recommended or authorized system operation. System operation may be terminated if a condition inconsistent with recommended or authorized system operation is detected. Such compliance apparatus may include an electronic scale for determining the weight of the waste loaded into the receiver compartment, a metal detector, or a sensor for determining if the decontaminating disinfectant is a recommended or authorized disinfectant. A communications link may be provided one or more systems to transmit information to a central station to deliver updates or commands associated with the recommended or authorized operation of each system.

19 Claims, 5 Drawing Sheets

(51) Int. Cl.
   *B02C 23/08*  (2006.01)
   *B02C 23/40*  (2006.01)
   *B02C 25/00*  (2006.01)
   *A61L 11/00*  (2006.01)
   *B02C 19/00*  (2006.01)
   *B02C 23/12*  (2006.01)
   *B02C 23/18*  (2006.01)
   *A61L 2/18*   (2006.01)
   *B09B 3/00*   (2006.01)

(52) U.S. Cl.
   CPC ............... *B02C 23/18* (2013.01); *B02C 23/36* (2013.01); *B02C 23/40* (2013.01); *B02C 25/00* (2013.01); *B09B 3/0075* (2013.01)

(56) References Cited

U.S. PATENT DOCUMENTS

| | | | |
|---|---|---|---|
| 4,884,756 A | 12/1989 | Pearson | |
| 5,054,696 A | 10/1991 | Mennel et al. | |
| 5,083,712 A * | 1/1992 | Askew et al. | 241/16 |
| 5,186,397 A | 2/1993 | Orlando | |
| 5,346,142 A | 9/1994 | Miller et al. | |
| 5,427,737 A * | 6/1995 | Glazer et al. | 422/26 |
| 5,516,049 A | 5/1996 | Zoncada | |
| 5,520,888 A | 5/1996 | Berndt | |
| 5,533,681 A | 7/1996 | Riley | |
| 5,568,895 A * | 10/1996 | Webb et al. | 241/16 |
| 5,570,845 A | 11/1996 | Lewis et al. | |
| 5,620,654 A * | 4/1997 | Mosenson | 422/28 |
| 5,799,883 A | 9/1998 | Lewis et al. | |
| 5,830,419 A | 11/1998 | Held et al. | |
| 6,042,802 A * | 3/2000 | Drake | 423/477 |
| 6,186,428 B1 | 2/2001 | Robinson et al. | |
| 6,494,391 B2 * | 12/2002 | Mosenson et al. | 241/36 |
| 7,360,730 B2 | 4/2008 | Brown | |
| 7,416,142 B2 * | 8/2008 | Baker et al. | 241/99 |
| 7,533,835 B2 * | 5/2009 | Hanson | 241/33 |
| 7,748,657 B1 | 7/2010 | Goodman | |
| 7,767,142 B1 * | 8/2010 | Smith et al. | 422/37 |
| 8,567,702 B2 * | 10/2013 | Kulesa et al. | 241/19 |
| 2008/0008635 A1 * | 1/2008 | Jakobi et al. | 422/291 |
| 2010/0278688 A1 | 11/2010 | Tanaka et al. | |
| 2010/0301147 A1 | 12/2010 | Harkess et al. | |
| 2010/0314221 A1 * | 12/2010 | Garberson et al. | 198/617 |
| 2011/0071230 A1 | 3/2011 | Ji | |
| 2013/0098400 A1 * | 4/2013 | Nguyen et al. | 134/18 |

FOREIGN PATENT DOCUMENTS

| | | |
|---|---|---|
| EP | 0662346 | 3/2001 |
| JP | 06-039004 | 2/1994 |
| WO | WO92/04920 | 9/1992 |
| WO | WO93/06418 | 4/1993 |
| WO | WO99/62566 | 12/1999 |
| WO | WO00/67808 | 11/2000 |
| WO | WO02/22270 | 3/2002 |
| WO | WO02/062479 | 8/2002 |
| WO | WO-2006100191 | 9/2006 |
| WO | WO-2009064538 | 5/2009 |

* cited by examiner

US 9,393,569 B2

INTEGRATED MEDICAL WASTE MANAGEMENT SYSTEM AND OPERATION

REFERENCE TO RELATED APPLICATION

This application claims priority from U.S. Provisional Patent Application Ser. No. 61/585,022, filed Jan. 10, 2012, the entire content of which is incorporated herein by reference.

FIELD OF THE INVENTION

This invention relates generally to medical waste management and disposal and, in particular, to an integrated system with numerous improvements and interlocks to encourage safe and proper operation.

BACKGROUND OF THE INVENTION

Medical waste, as generated in medical, veterinary, dental and laboratory facilities, includes a wide variety of materials and substances, including bandages, gloves, infusion bags, hypodermic needles, syringes, products of dialysis, testing vials, plastic bags, tubes, containers, blood, human and animal wastes. Medical waste must be disposed in a safe, expeditious and hazard-free manner. In large medical facilities, the medical waste is generally collected at a central location and treated by incineration or steam disinfection before disposal into a landfill. Such processes are not only costly, but may also be environment-unfriendly in pollution generated during treatment, their reliance upon transportation of the waste to an offsite treatment facility, and in the less-than-optimal use of environmental un-renewable resources.

Because of the different types of medical waste to be disposed, a number of devices have been developed which include shredders for shredding the medical waste in order to reduce the overall volume and to facilitate sterilization or disinfection. U.S. Pat. Nos. 5,620,654 and 6,494,391, the entire content of both being incorporated herein by reference, relate to equipment having a footprint with sufficiently small dimensions facilitating installation in hospital departments or wards, laboratories or clinics for on-site treatment, disinfection, and localized disposal. Such systems relate particularly to a method and equipment for automatically grinding, sanitizing and neutralizing both acid and basic medical waste, and for disposing it after treatment.

The '654 patent discloses equipment mounted in a tightly closable housing provided with charge and discharge openings. The housing contains a shredder for comminuting the inserted raw waste and for conveying the shredded material to a mixing vessel where it is diluted with water and thoroughly mixed. A container storing tubes filled with several kinds of sanitizing materials is configured to dispense the required number and kinds of tubes into the shredder in accordance with the pH value of the mixture. The pH level is communicated to a selective valve mechanism by a sensor attached to the vessel. The equipment further includes a pump for recirculating liquid from the vessel to the shredder, and a pump for draining fluid from the mixing vessel. A conveyor (25) conveys the sanitized waste out of the vessel and out of the housing. Electronic and control equipment is provided for operating the various components.

While the invention described in the '654 patent has been incorporated in commercial settings, such apparatus is relatively large and costly, and therefore has been found to be more suitable for relatively large medical facilities, such as large-size and medium-size hospitals. The '391 patent improves upon the teachings of the '654 patent by providing medical waste treatment equipment suitable to relatively small facilities, such as medical, dental, dialysis and veterinary clinics. To achieve this goal, such equipment includes a treatment vessel having an open top, pivotal within a housing, between a waste-loading position, a waste-treating position and a waste-removing position. In the waste-loading position, the open top of the treatment vessel is aligned with the housing inlet for receiving the waste. In the waste-treating position, the waste is shredded by a shredder unit disposed within the treatment vessel, and in the waste-removing position, the open top of the vessel is aligned with the housing outlet for removing the shredded waste. The apparatus further may additionally include a compactor head for compacting the waste within the treatment vessel, a water feed line, and a disinfectant feed line, for feeding water and a disinfectant into the treatment vessel, and a mixer for mixing with the waste while it is being compacted and shredded.

SUMMARY OF THE INVENTION

This invention relates generally to medical waste management and disposal and, in particular, to an integrated system with numerous improvements and interlocks to encourage safe, unmanned automatic and proper operation. A medical waste treatment system constructed in accordance with the invention includes an enclosure having a receiver compartment for loading medical waste to be treated. The receiver compartment feeds a motor-driven shredder operative to shred the waste placed in the receiver compartment. A tank receives a decontaminating disinfectant which is mixed with the waste loaded into the receiver compartment. A pump recirculates the waste and disinfectant mixture through the shredder until the particle size of the decontaminated waste is reduced to a desired granular consistency, at which point the mixture is output through a discharge port.

Compliance apparatus is provided as part of the system for determining if the waste, the decontaminating disinfectant, or the status of the system are consistent with recommended or authorized system operation. In accordance with one embodiment, the compliance apparatus includes an electronic scale for determining if the weight of the waste loaded into the receiver compartment exceeds a predetermined limit of the system's capacity. If the weight exceeds the predetermined limit, an error or alarm may be generated and/or an interlock may be activated preventing system operation. Such an error, alarm or interlock may be responsive to any of the compliance apparatus disclosed herein.

The compliance apparatus may include a metal detector for determining if the waste loaded into the receiver compartment contains any metal objects incompatible with the motor-driven shredder. The compliance apparatus may include a sensor for determining if the decontaminating disinfectant is a recommended or authorized disinfectant. In the preferred embodiment, the decontaminating disinfectant is received in a containing having an RFID tag or computer-readable code, and the system is operative to determine if the decontaminating disinfectant is a recommended or authorized disinfectant by the RFID tag or code detected or imaged by the sensor.

The compliance apparatus may further comprise a sensor for detecting whether the shredded waste slurry has sufficient water content, and a water filling valve or pump for adding water to the slurry until the sensor detects that the water-to-solid ratio of the slurry reaches a desired ratio. A sensor may additionally be provided for detecting whether the disinfectant is at or below a predetermined level in parts per million, with a pump for adding water or other liquid to the medical waste to ensure that the disinfectant is at or below the predetermined level prior to discharge of the effluent into the sewer; thereby ensuring compliance with local discharge regulations and ordinance for discharge of disinfectants.

The compliance apparatus may further include a software algorithm as part of the system's controller for detecting whether the recommended or authorized disinfectant has been placed into the device, with said software relying upon a database of randomly generated multi-digit numbers that correspond with a valid disinfectant identification numbers which are printed on the labels of recommended or authorized disinfectants.

The compliance apparatus may include a communications link enabling one or more systems to transmit information to a central station for determining if the waste, the decontaminating disinfectant, or the status of the systems are consistent with recommended or authorized system operation. The communications link to the central station is wired or wireless. The communications link to the central station may form part of a bidirectional communication link enabling the central station to deliver updates or commands associated with the recommended or authorized operation of each system. Such updates may include, for example, reminders regarding preventative maintenance or changes in regulatory rules, laws, ordinances or guidelines.

The system may include a separator unit to receive the decontaminated, granular waste from the discharge port, remove liquid from the mixture, and transfer the waste to a filter bag or other receptacle for disposal purposes. A conduit may be provided for discharging the liquid removed from the decontaminated, granular waste to a drain, with the compliance apparatus in this case including a pump for adding a specified amount of water to the discharged liquid to ensure compliance with local sanitary sewer ordinances or regulations.

The treated waste de-watering separator unit includes a conveyor or chute, and a heated or non-heated air knife may be disposed along the conveyor or chute to remove liquid from the shredded granular material that may otherwise remain due to surface tension. The system may further including a discharge valve on the discharge port that is closed while the waste is recirculated through the shredder, and wherein the valve is opened to convey the decontaminated, granular waste to the separator unit.

To enhance the biodegradability of the decontaminated waste, the system may further include compliance apparatus for the use of stabilized hydrogen peroxide ($H_2O_2$) as a fully biodegradable disinfectant. An independent, dedicated hydrogen peroxide ($H_2O_2$) generator may be provided to produce the $H_2O_2$ added to the untreated waste. A viewing window may be included in the systems' waste receiver enabling an operator to view the waste being treated.

DETAILED DESCRIPTION OF THE INVENTION

This invention provides several distinct improvements to on-site medical waste treatment systems, with sensors, interlocks, communications links and other features for determining if the waste itself, the decontaminating disinfectant used in the process, or the status of the system are consistent with recommended or authorized system operation.

Figure 1:
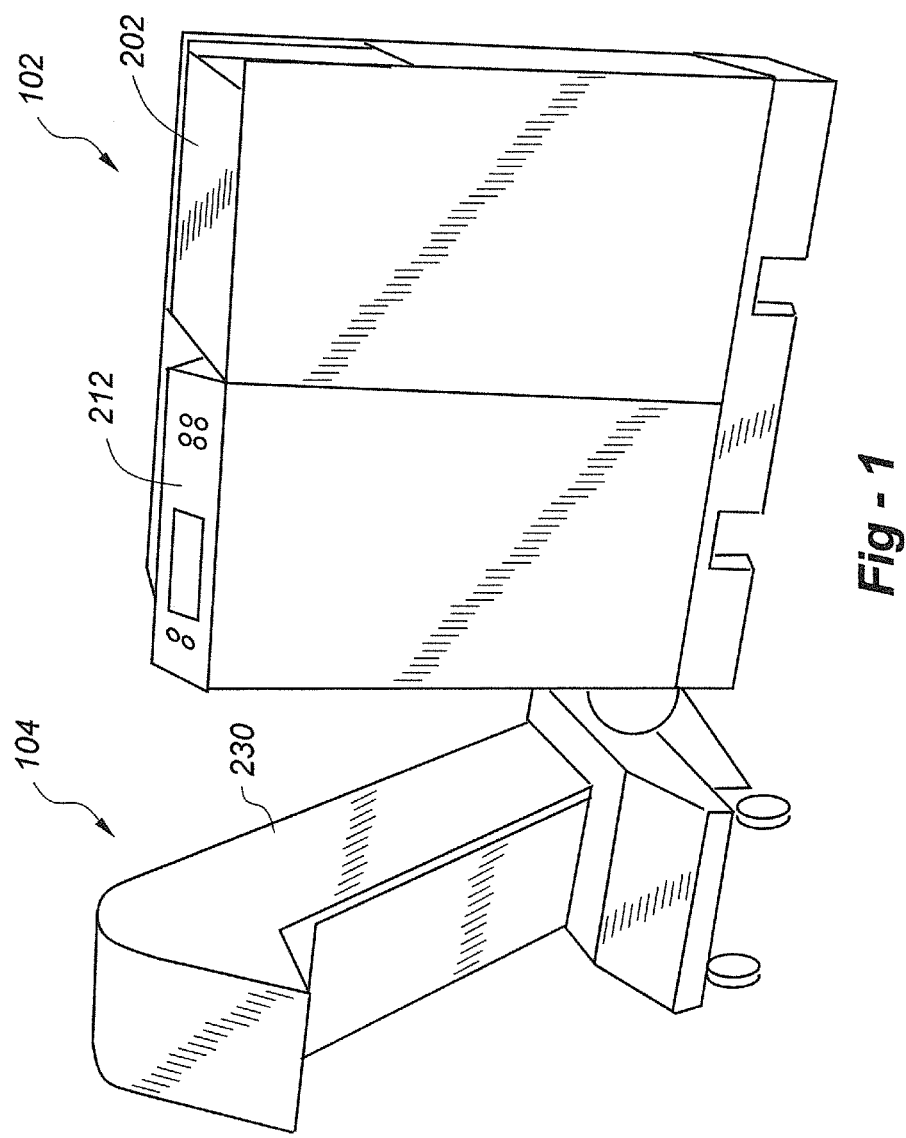
FIG. 1 illustrates a medical waste treatment and disposal system according to the present invention.

FIG. 1 illustrates a medical waste treatment and disposal system to which the inventions disclosed herein are applicable, with the understanding that some or all of the various improvements and modifications are applicable to other medical waste systems, including those described in the Background section, above. Moreover, the various improvements and modifications are patently distinct in the sense that they may be used individually or in any combination thereof for improved performance, reporting, maintenance, safety or other operational characteristics.

Figure 2:
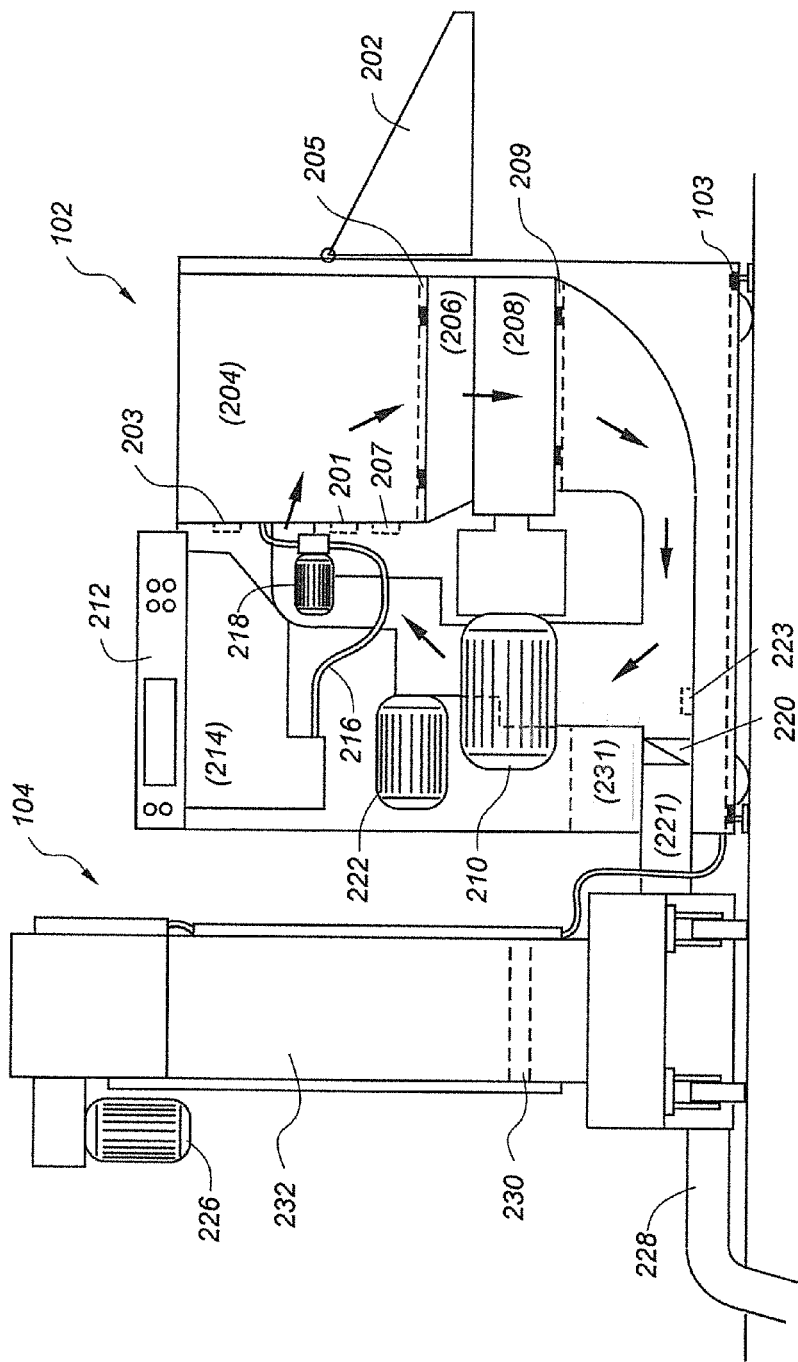
FIG. 2 is a front view of a shredding/decontamination unit and companion separator unit with the cover of the main unit being removed to reveal important subsystems.

The system of FIG. 1 includes a main unit 102 that receives shreds and decontaminates the medical waste. A separator unit 104 removes moisture and transfers the treated waste into a filter bag within a non-infection garbage container or wagon (not shown) for removal. FIG. 2 is a front view of the two units with the cover main unit 102 removed to reveal the inner workings. The operator opens loading door 202 and places untreated waste in a receiver compartment 204. The receiver compartment 204 communicates with a press section 206 which feeds a shredder 208 driven by electric motor 210.

After the untreated waste is placed in the receiver compartment 204, the loading door 202 is closed and a "start" cycle is initiated with control panel 212. The control panel 212 communicates with a system controller which, in turns, commands and directs overall operation of the equipment. The first phase of the decontamination process is the introduction of water and a decontaminating detergent into the receiver compartment 204. The recommended decontaminating disinfectant is a proprietary product called SterCid, available SteriMed Medical Waste Solutions, Inc. of Farmington Hills, Mich. The concentration of SterCid during the disinfection and treatment cycle is preferably 0.5% of the total volume of liquids. The SterCid solution is contained in tank 214 and fed into compartment 204 through tubing 216 via electric pump 218.

The next step of operation is the "shred" phase. During this phase, cutting teeth in shredder 208 shred and reduce the particle size of the material to a granular consistency, with particle size being in the range of 1 to 2.5 cm (¼ to ½ inch). During the shredding operation, discharge valve 220 is closed and the mixture is recirculated from the shredder 208 back into the receiver 204 in the loop identified by the arrows until the desired particle size is achieved using pump motor 222.

The final step of the operation is the "discharge" phase, which takes approximately 1 minute. The discharge valve 220 is opened, and the treated waste is transferred to the separator unit 104 through discharge port 221, then discharged into a filter bag or alternative receptacle. The treated material is drawn up through the separator 104 using motor 226 where the material is rinsed. The liquid from the rinsing process drains into the sewage system though conduit 228. Once the filter bag, garbage container or wagon is full, the treated material can be disposed of as ordinary 'black bag' waste.

The improvements and modifications which are the subject of this invention will now be described in detail in the subsequent sections.

Smart Receiver Weight Sensor

A first improvement relates to proper loading of the receiver compartment 204 with appropriate medical waste to be treated and shredded. According to this aspect of the invention, the receiver compartment 204 will be outfitted with one, two or three types of integrated sensors: (i) an integrated pressure transducer or load cell module; (ii) an integrated metal detector; and/or (iii) a radiation detector.

The pressure transducer load cell module provides the system controller with information as to the weight of the medical waste which is placed into the system by the operator at the start of the cycle. The transducer itself may be located immediately below the receiver compartment 204 at 205; under the shredder 208 and motor 210 at 209; or under the entire main unit 102 at 103 so long as the change in weight due to the loaded contents may be accurately determined.

Weight determination offers significant advantages. First, the operator is proactively notified of accidental overload of machine prior to start of automatic cycle. If excessive waste is loaded, the machine will not start the initial cycle, and operators will be provided with an "overload" warning when they attempt to start the automatic cycle. The weight of each machine cycle is also stored in memory and printed by a system printer along with all other parametric data associated with each operational cycle.

The weight of the untreated medical waste is automatically communicated to the system controller to eliminate need for a side-car stand-alone weight scale in markets such as the United Kingdom and Mexico where users of on-site medical waste processors must record starting weight of the untreated medical waste. The weight determination also allows commercial treatment facilities and medical office building installations to track the weight of each machine cycle for immediate billing to specific waste generator clients by the weight of waste loads, and tracking and reporting of waste that was treated by the system for regulatory compliance. The weight determination also ensures that the system will not attempt to treat medical waste which exceeds the maximum weight upon which the system's microbiological efficacy had been validated.

Smart Receiver Metal Detector

The integrated metal detector module 207 provides the system controller with information regarding whether the untreated waste contains too large of a metal object, such as a non-shredable medical implant or surgical tool, which would trigger automatic shredder overload detection during the automatic cycle. This improvement is advantageous since untreated waste is often loaded in "red bags" that do not readily reveal their contents. This sensor system informs the operator prior to the start of the shredding phase of the system that the red bag which has been placed into the treatment vessel contains "too large" of a metal object which has been mistakenly disposed of into the red bag waste steam before they start the automatic cycle.

Smart Receiver Color Detector

As a further option, the receiver compartment 204 may also contain an optical sensor 203 to detect the color of the loaded material. Such a feature would, for example, allow red bags of material while rejecting yellow or white containers as these signify dangerous chemicals that should not be added to the system due to certain regulatory restrictions on the treatment of waste which has been color coded by waste category.

Smart Receiver Radiation Detector

As further option, the receiver compartment 204 may also contain a radiation sensor 201 to detect the presence of waste containing radioactive materials, such as onocological waste. Such a feature would, for example, prevent the automatic treatment process from being started by the operator if certain dangerous waste materials that were not intended or approved by regulatory agencies for use in the system were inadvertently loaded into the system.

Smart Receiver Viewing Window

The smart receiver aspect of the invention would also include an integrated viewing window on the receiver compartment 204 and/or loading door 202 which allows both operators and technicians to view the inside of the waste receiver during the actual treatment process. In addition to careful monitoring of the treatment process, this aspect of the invention facilitates technical troubleshooting during machine manual operation, such as back-flush routines to clear a jammed shredder.

Smart Shredder

The smart shredder is a sensor enabled monitor interfaced to the discharge valve 220. The sensor 223 installed in the region of the valve detects whether the shredded waste slurry has sufficient liquid content to ensure that it can flow freely through the system's waste recirculation system. If the sensor detects that the shredded waste slurry has a high solids content, the smart shredder will be commanded to stop shredding, and the slurry will be automatically diluted water and/or disinfectant until the sensor detects that the water-to-solid ratio of the waste approximates a 50:50 ratio to ensure smooth movement of the waste stream through the waste recirculation pump 222.

Smart Discharge

To ensure compliance with certain local sewer ordinances or regulations, software is used to ensure that specific amounts of fresh water are added to the liquid effluent which contains the disinfectant to ensure concentration control during its discharge into the sanitary drain. This aspect of the invention allows the operator to set up and define into the system's controller the required discharge performance of the machine based upon an easy to interpret software setting in parts per million (ppm). Once the required ppm setting for the discharge is entered into the system controller, the machine will discharge the diluted chemical disinfectant automatically to achieve this ppm discharge limit by automatically injecting into the discharge stream the required amount of cold water to dilute the effluent discharge to the ppm set point.

Smart Discharge Air Knife

To ensure that the product in the separator 104 is sufficiently dry, and to comply with certain regulatory limits for the level of free liquids in a solid waste stream, a further aspect of the invention includes a heated or non-heated air knife 230 disposed along the chute 232 of the separator 104 to remove free liquids from the shredded granular material that may otherwise remain due to surface tension. Such removed liquid will then flow back down the chute and out drain 228.

Communications Capabilities

Figure 3A:
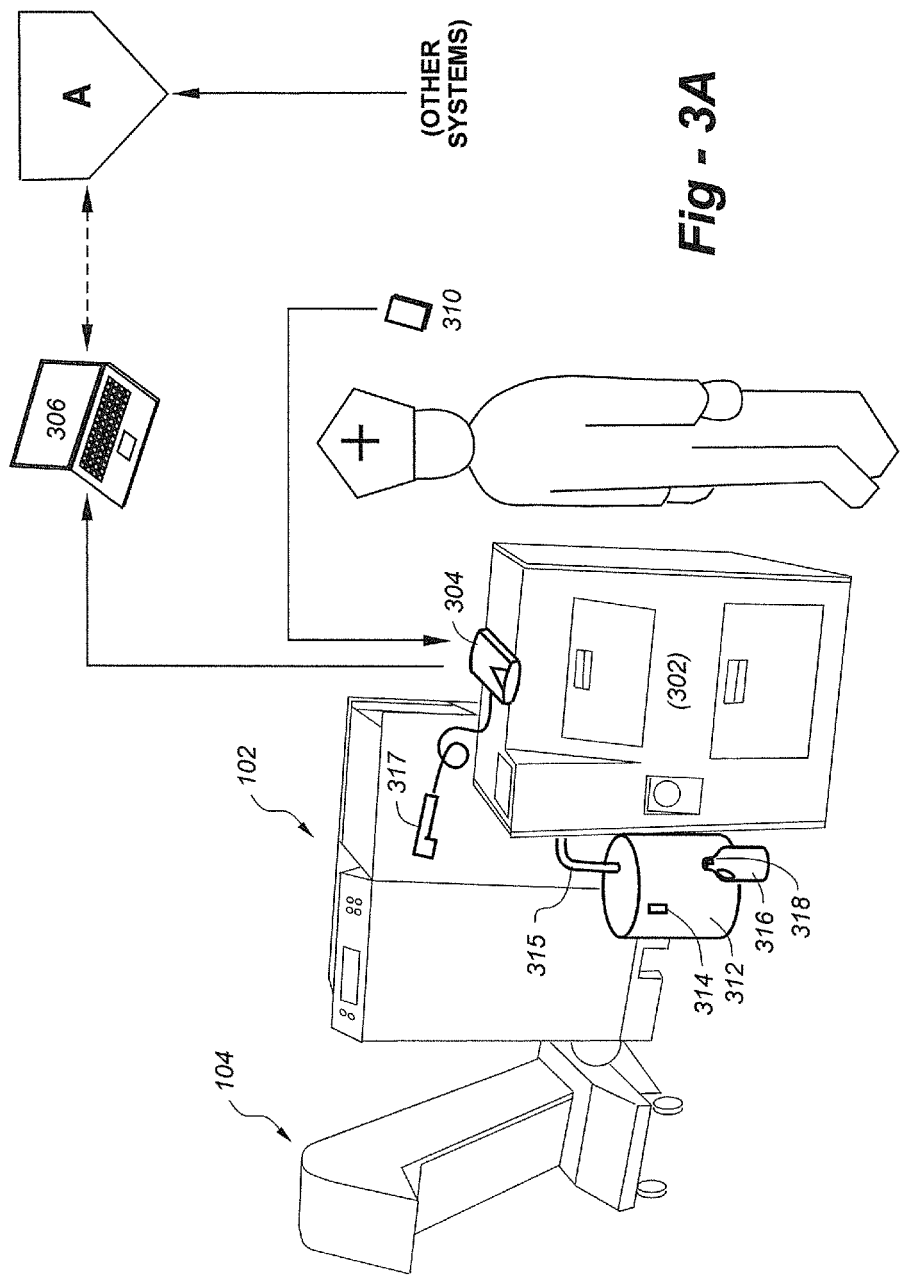
FIG. 3A illustrates a stand-alone system in wired or wireless communication with a central station.
Figure 3B:
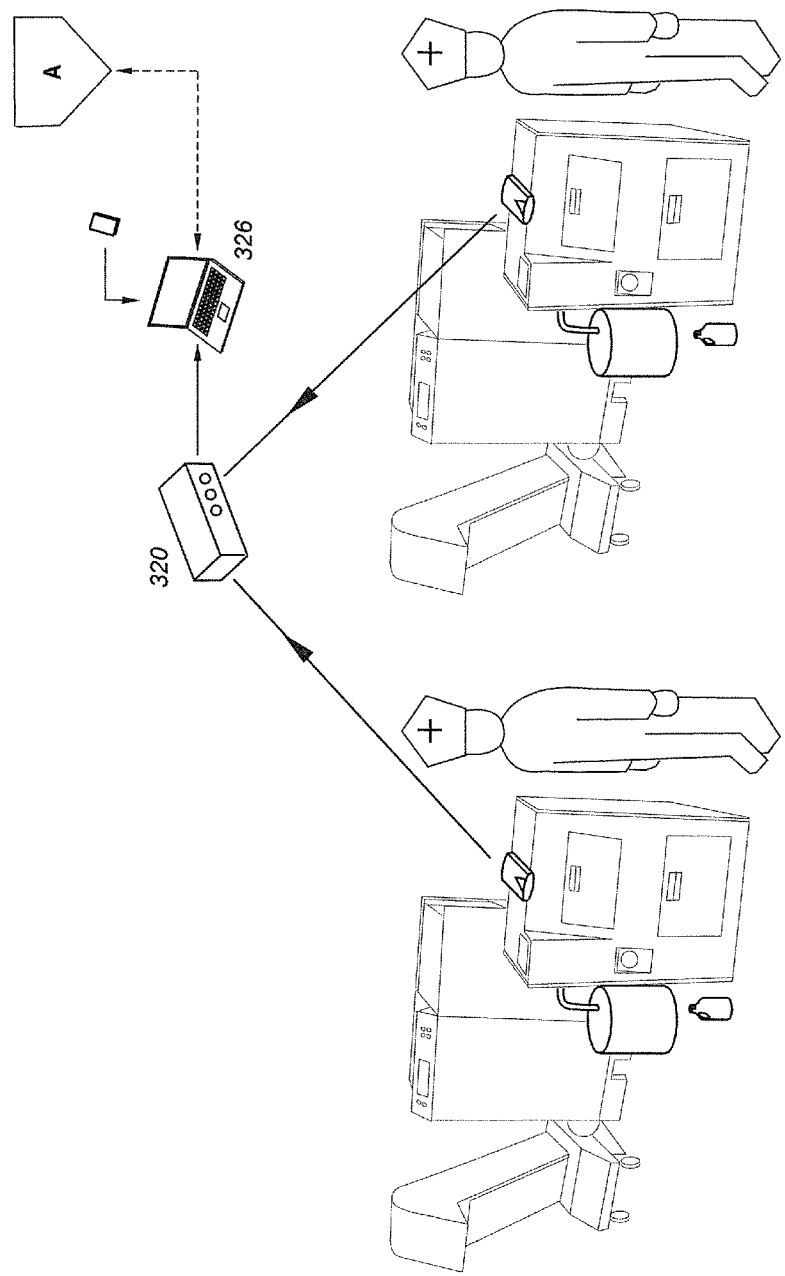
FIG. 3B shows a multi-system configuration with a partially wired communication link to a central station.
Figure 3C:
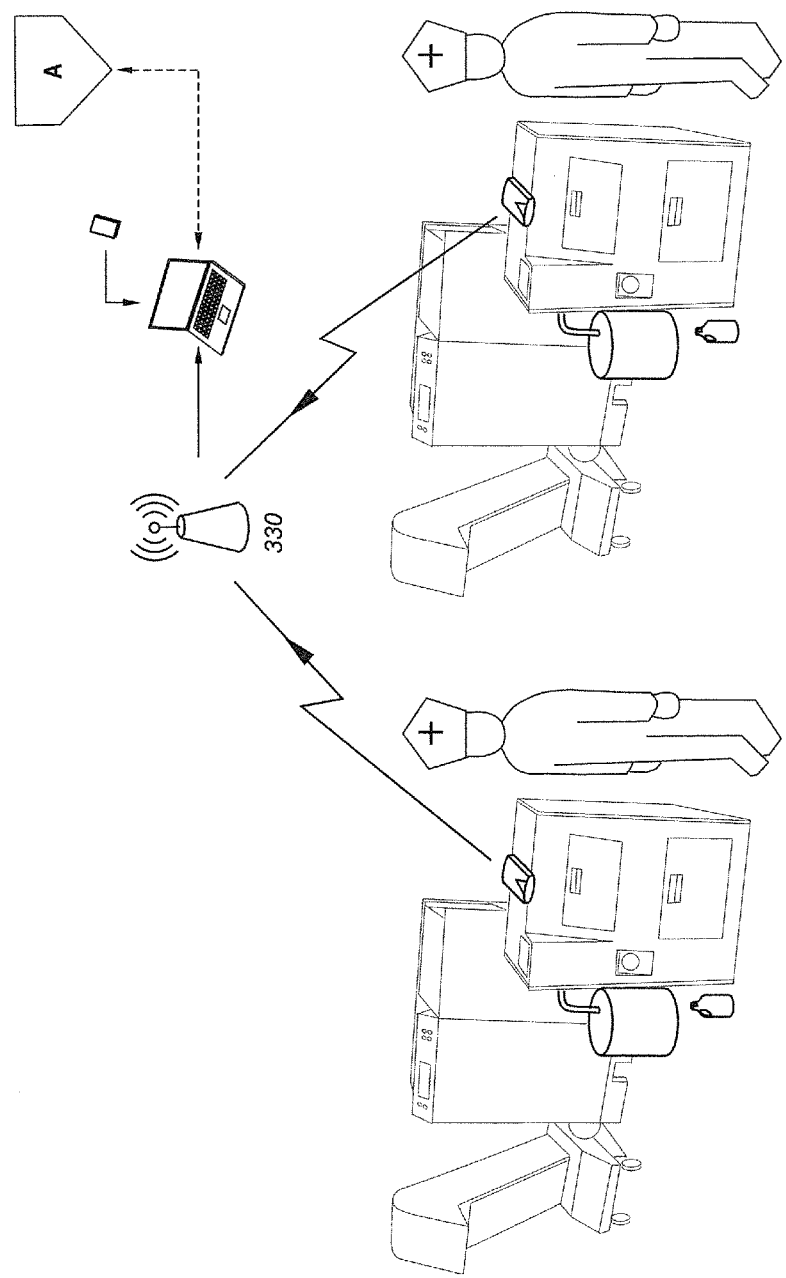
FIG. 3C depicts a multi-system configuration with wireless connections to a central station.

In accordance with this aspect of the invention, the waste management system is in communication with a central station to send and/or receive compliance data, updates commands or other information. FIG. 3A illustrates a stand-alone system in communication with a central station "A." FIG. 3B illustrates a multi-system configuration with a partially wired communication link to a central station, and FIG. 3C depicts a multi-system configuration with wireless connections to a central station. Although in these drawings communications and other features are represented in conjunction with a "junior" system 302 that is not equipped with a separator unit, the reader will appreciate that all of the capabilities described herein apply equally well to system 102 with separate separator unit 104.

In the configuration of FIG. 3A, communication is mediated through computer 306, which may be a separate, conventional piece of equipment or integrated into the system 102 or 302. The configuration of FIG. 3B includes an Ethernet hub or USB node 320 which again may communicate with central station "A" through computer 326. While the connections to the hub 320 are assumed to be hard-wired, the rest of the connection(s) may be wired or wireless. The environment of FIG. 3C uses a wireless access point 330, whereby all network communications in this case are wireless. In all configurations it may be assumed that station "A" may be in communication with other systems, whether stand-alone or tandem wired/wireless implementations.

A preferred arrangement uses wireless, bidirectional links enabling constant communication with the central station or main office using, for example, a 12-channel cellular communication module. This capability allows the system to communicate in real time with the central office and/or the user's biomedical technical department. The use of a cellular radio channel addresses the need for a hardwire connection to the equipment, and allows for mobile application and placement of equipment in facilities where hardwired installation and/or an Internet connection is problematic. Other communications equipment and protocols, including WiFi, may alternatively be implemented.

The networking allows communications, including information regarding the number of cycles attempted and completed by the equipment, automated billing for pay-per-click applications, equipment inhibit by remote control for buy-here pay here equipment financing, automatic consumables re-ordering, equipment performance details and the maintenance status of each piece of equipment. The capability enables proactive dispatch of technicians to improve equipment availability, while providing reliable time stamping of equipment failure events for repair technician performance tracking. Up to 12 key elements of parametric data will be sent using the telecommunications network utilizing both SMS and email messaging, and/or GPRS data using radio packet protocol.

Bi-directional control also allow signals from the central station to control the equipment's key functions such as system reset and system shut down, while allowing customers on pay-per-click equipment acquisition models to report on their daily use of equipment automatically. Bidirectional control features also allow for the equipment to be remotely disabled by the central station operator for equipment users who may have become delinquent in making monthly equipment use payments to the equipment owner; who do not use the approved decontaminating detergent; who use the equipment in an unapproved manner, and so forth.

"E-Regulatory" Compliance

For installations where waste treatment logs are to be maintained, all treatment data may be dispatched wirelessly to each client via the wireless communication system. Daily, weekly, monthly or annual treatment logs may be stored online at a server, and can be e-mailed to each client as a PDF or other appropriate file type, thereby replacing the need for printed paper treatment logs which are generated by the sidecar stand-alone printer. PC connectivity, as opposed to Internet connectivity, is also available, allowing the unit to send parametric and treatment logs directly to a connected PC in the facility for regulatory reporting.

Routine Preventive Maintenance Reminder Services

In cases where the equipment is covered by a service contract after the end of a warranty period, customers must perform certain routine preventive maintenance. The bi-directional wireless communication capability and interface to the equipment allows for service reminders to be sent to and from the equipment so that maintenance service can be acted upon in a timely manner at the deployed site. Once the equipment maintenance is performed, and a particular service reminder warning is turned off on the equipment, these notices are automatically sent back to the central office where the record of maintenance is maintained electronically to verify compliance with the contract, and to record maintenance for regulatory compliance in markets where service records must be recorded.

Treatment Chemical Compliance

The waste treatment process includes the equipment itself, along with certain registered proprietary chemicals (i.e., Ster-Cid) for use exclusively in the waste treatment devices. In certain overseas markets, the laws of these countries allow for substitution of the disinfectant chemical used in the waste treatment equipment; albeit a violation of warranty and contractual agreements. The use of substitute chemicals in overseas markets is a violation of the approved use of the equipment and results in loss of revenues to the authorized supplier, as the monthly recurring revenue from disinfectant sales is lost. The use of substitute chemicals, either through accidental or intentional use, may also damage certain components of the treatment devices and result in unapproved use of the equipment in accordance with certain regulatory approvals and permits.

To prevent accidental or intentional chemical counterfeiting or usage, a Radio Frequency Identification Device (RFID) or computer-readable code is included with authorized treatment chemical containers. In FIG. 3A, a larger container 312, which may feed either systems 102, 302 through a conduit such as line 315, includes an RFID tag 314 which is automatically detected by reader/controller 304. The container 316 may also include a machine-readable code such as a bar code 318 read by a wand 317 interfaced to reader/controller 304. The reader/controller 304 may automatically act upon an unauthorized chemical usage, preventing system operation, for example, and/or the reader/controller 304 may communicate the unauthorized usage to the central station via the communication link(s).

The tag or code may be molded into the cap of the disinfection bottle, or affixed to the outside of the cap of the bottle using a tamper-evident label which will be destroyed when the bottle cap is opened. The appropriate reader is integrated into the system controller, and the controller software requires that the equipment read a valid tag or code from the chemical cap or container in order for the waste treatment process to continue. In this way, use of a chemical substitute without a scanable tag or code will prevent the machine from operating; hence any attempt to use a counterfeit chemical will be prevented.

This ChemLoc™ system, integrated into the system controller, ensures that only authentic SterCid disinfecting solutions are utilized in the treatment systems. System operation is blocked unless authentic disinfecting solution is utilized. The ChemLoc includes a unique tag (label) that can be automatically applied to each SterCid unit container at the time of container filling. This aspect of the invention may include a method for accumulation of all tag/label unique codes within a manufacturing (filling operations) batch and replication of this database to portable memory devices such as SanDisk non-volatile flash memory data cards that can be shipped to each customer site with the SterCid disinfecting solution containers. FIG. 3 illustrates three different operational options using portable database cards. In FIG. 3A, the card database 310 interfaces directly to reader/controller 304, whereas in FIGS. 3B, 3C, the database interfaces to the network computer.

The reader/controller system scans the disinfecting solution container tags/codes and authenticates the container as an authentic solution container through comparison of the tag (label) unique code to the SD data card internal database. The result of the comparison is communicated to a system controller comprised of either a personal computer (PC) or an industrial grade programmable logic controller (PLC) using the Internet or other form of connectivity.

To prevent accidental or intentional chemical counterfeiting or usage, a software-only method is also supported. In the software-only embodiment of this feature, the use of an RFID tag is not used. In this software only embodiment, the control system of the equipment includes a large database of read-only multiple digit chemical identification numbers. These numbers are produced by a random number generator using a certain algorithm that prevents the duplication of these security identification numbers. The database of randomly generated security identification codes is then used to print the same set of numbers onto the disinfectant container labels. The software system requires that the operator enter into the system controller a valid chemical/disinfectant identification number whenever the system requires additional disinfectant. The system will not operate if the operator enters an invalid chemical identification number into the system controller. The software in the system is designed in such a manner that when an operator enters a chemical identification numbers into the system control keypad, the system control then compares the identification number that was entered by the operator, with the list of pre-registered valid, randomly generated chemical identification numbers. If a valid chemical identification number is entered by the operator, the system will delete this identification number from the system's database of valid identification numbers to prevent reuse of this number in the future. If an invalid chemical identification number is entered, the system will become inhibited; requiring a single use password to be entered by the operator to allow system operation.

While the equipment and method are primarily intended as a process-use specific embodiment and not as a stand-alone general purpose waste shredder/disinfector, special application specific software may be included with the equipment for other unique markets, including the following:

Use by a medical waste hauler who collects waste generated by third party facilities and transports this collected waste to a central depot for processing.

Use by a whole blood collection unit operator, who must track each bag of "whole blood" units collected and then track precisely the date, time, and method of destruction of each blood unit which was determined to be unacceptable for re-distribution into the global blood supply.

Use by a mobile-deployed unit, such as a device placed on a moving truck or shipboard naval/cruise ship unit, which requires that the equipment be automatically secured for movement and detection movement as part of the machine's automatic cycle.

Use of the equipment in a "common area" of a facility such as a medical office building (MOB) where several users have access to the equipment for waste treatment; much like a photocopier, and use of the equipment by each user/operator must be identified, controlled, restricted, and even automatically recorded by the system to prevent unauthorized use, or the creation of automatic usage invoices, etc.

Enhanced Biodegradability

At the present time, SterCid disinfectant is 94% biodegradable. To increase this value to 100%, additional formulation of liquid-based disinfectants can be used. One such formulation is stabilized hydrogen peroxide ($H_2O_2$). Another solution may be added $H_2O_2$ is acetic acid, which improves the shelf life of the hydrogen peroxide based disinfectant but will also produce an acidic result. One of the problems with externally supplied $H_2O_2$, however, is that it rapidly breaks down and loses its effectiveness. As a further aspect of this invention, the system may include an on-board $H_2O_2$ generator 231 utilizing various known or yet-to-be-developed techniques.

As one example, hydrogen peroxide may be generated using an electrochemical cell having a gas diffusion electrode as the cathode (electrode connected to the negative pole of the power supply) and a platinized titanium anode. The cathode and anode compartments are separated by a readily available cation-exchange membrane (i.e., Nafion® 117). The anode compartment is fed with deionized water. Generation of oxygen is the anode reaction. Protons from the anode compartment are transferred across the cation-exchange membrane to the cathode compartment by electrostatic attraction towards the negatively charged electrode. The cathode compartment is fed with oxygen, and hydrogen peroxide is generated by the reduction of the oxygen. Water may also be generated in the cathode. A small amount of water is also transported across the membrane along with hydrated protons transported across the membrane. Generally, each proton is hydrated with 3-5 molecules. The output is hydrogen peroxide as a high-purity aqueous solution which may be added to the SterCid disinfectant mixture or replace SterCid as desired.

We claim:

1. A medical waste treatment system, comprising:
   an enclosure having a receiver compartment for loading medical waste to be treated;
   a motor-driven shredder operative to shred the waste placed in the receiver compartment;
   a tank for receiving a decontaminating disinfectant;
   a conduit for delivering the decontaminating disinfectant to mix with the waste loaded into the receiver compartment;

a pump for recirculating the waste and disinfectant mixture through the shredder until the particle size of the decontaminated waste is reduced to a desired granular consistency;

a discharge port for outputting the decontaminated waste having the desired granular consistency; and compliance apparatus including a sensor for detecting whether the shredded waste slurry has sufficient water content, and a pump for adding water to the slurry until the sensor detects that the water-to-solid ratio of the slurry reaches a desired ratio.

2. The medical waste treatment system of claim 1, wherein the compliance apparatus includes an electronic scale for determining if the weight of the waste loaded into the receiver compartment exceeds a predetermined limit.

3. The medical waste treatment system of claim 2, further including an interlock for automatically recording the weight of the waste which was loaded into the system and to prevent system operation if the weight exceeds the predetermined limit.

4. The medical waste treatment system of claim 1, wherein the compliance apparatus includes a metal detector for determining if the waste loaded into the receiver compartment contains any metal objects incompatible with the motor-driven shredder.

5. The medical waste treatment system of claim 4, further including an interlock for preventing system operation if any metal objects incompatible with the motor-driven shredder are detected.

6. The medical waste treatment system of claim 1, wherein the compliance apparatus further includes a sensor for determining if the decontaminating disinfectant is a recommended or authorized disinfectant.

7. The medical waste treatment system of claim 6, wherein:
the decontaminating disinfectant is received in a container having an RFID tag or computer-readable code; and
the system is operative to determine if the decontaminating disinfectant is a recommended or authorized disinfectant by interpreting the RFID tag or code received by the sensor.

8. The medical waste treatment system of claim 1, wherein the compliance apparatus further includes:
a sensor for detecting whether the disinfectant is at or below a predetermined level in parts per million prior to the discharge of diluted disinfectant into the sewer system; and
a pump for adding water or other liquid to the medical waste to ensure that the disinfectant is at or below the predetermined discharge requirement level.

9. The medical waste treatment system of claim 1, wherein the compliance apparatus includes a communications link enabling one or more systems to transmit information to a central station for determining if the waste, the decontaminating disinfectant, or the status of the systems are consistent with recommended or authorized system operation.

10. The medical waste treatment system of claim 9, wherein the communications link to the central station is wired or wireless.

11. The medical waste treatment system of claim 9, wherein the communications link to the central station is part of a bidirectional communication link enabling the central station to deliver updates or commands associated with the recommended or authorized operation of each system.

12. The medical waste treatment system of claim 11, wherein the updates from the central station include reminders regarding preventative maintenance.

13. The medical waste treatment system of claim 1, further including a separator unit to receive the decontaminated waste from the discharge port, remove liquid from the mixture, and transfer the waste to a filter bag or other receptacle for disposal purposes.

14. The medical waste treatment system of claim 13, further including:
a conduit for discharging the liquid removed from the decontaminated waste to a drain; and
wherein the compliance apparatus includes a pump for adding a specified amount of water to the discharged liquid to ensure compliance with local sanitary sewer ordinances or regulations.

15. The medical waste treatment system of claim 13, wherein:
the separator unit includes a conveyor or chute; and
a heated or non-heated air knife disposed along the conveyor or chute to remove liquid from the shredded granular material that may otherwise remain due to surface tension.

16. The medical waste treatment system of claim 13, further including a discharge valve on the discharge port that is closed while the waste is recirculated through the shredder, and wherein the valve is opened to convey the decontaminated, granular waste to the separator unit.

17. The medical waste treatment system of claim 1, wherein the compliance apparatus adds hydrogen peroxide ($H_2O_2$) to the waste to enhance the biodegradability of the decontaminated waste.

18. The medical waste treatment system of claim 17, further including an independent, dedicated hydrogen peroxide ($F_2O_2$) generator for producing the $H_2O_2$ added to the decontaminated waste.

19. The medical waste treatment system of claim 1, further including a viewing window allowing an operator to view the waste being treated.

\* \* \* \* \*